US008401146B2

(12) United States Patent
Vorhees (10) Patent No.: US 8,401,146 B2
(45) Date of Patent: Mar. 19, 2013

(54) CONVEYER BELT WITH OPTICALLY VISIBLE AND MACHINE-DETECTABLE INDICATORS

(76) Inventor: R. John Vorhees, Clearfield, UT (US)

(*) Notice: Subject to any disclaimer, the term of this patent is extended or adjusted under 35 U.S.C. 154(b) by 380 days.

(21) Appl. No.: 12/834,182

(22) Filed: Jul. 12, 2010

(65) Prior Publication Data

US 2011/0007871 A1    Jan. 13, 2011

Related U.S. Application Data

(60) Provisional application No. 61/225,033, filed on Jul. 13, 2009.

(51) Int. Cl.
*G01N 23/04* (2006.01)
(52) U.S. Cl. ......................................................... 378/57
(58) Field of Classification Search .................. 378/57, 378/62; 250/453.11, 492.1; 198/339.1
See application file for complete search history.

(56) References Cited

U.S. PATENT DOCUMENTS

| 3,547,121 | A | * | 12/1970 | Cherry | 604/116 |
| 3,639,764 | A | * | 2/1972 | Olson et al. | 378/193 |
| 3,777,643 | A | * | 12/1973 | Asbelle et al. | 396/5 |
| 5,052,035 | A | * | 9/1991 | Krupnick | 378/163 |
| 6,396,903 | B1 | | 5/2002 | Wenstrup | |
| 2004/0062346 | A1 | * | 4/2004 | Fernandez | 378/41 |

FOREIGN PATENT DOCUMENTS

WO    WO 2010/112117    7/2010

* cited by examiner

*Primary Examiner* — Irakli Kiknadze
(74) *Attorney, Agent, or Firm* — Thorpe North & Western LLP (57) ABSTRACT

A method for correlating optically visible objects with objects detectable through a non-invasive imaging system is described. The method includes conveying an object on a conveyer belt through the non-invasive imaging system. The conveyer belt can include optically visible indicia and machine-detectable indicia. The object and the machine-detectable indicia can be displayed on a display in communication with the non-invasive imaging system. The machine-detectable indicia viewed on the display can be correlated with the optically visible indicia on the conveyer belt after the object has exited the non-invasive imaging system to identify the object.

19 Claims, 6 Drawing Sheets

CONVEYER BELT WITH OPTICALLY VISIBLE AND MACHINE-DETECTABLE INDICATORS

PRIORITY CLAIM

This application is based upon and claims the benefit of priority from U.S. Provisional Patent Application No. 61/225,033, filed Jul. 13, 2009, the entire contents of which is incorporated herein by reference.

BACKGROUND

Endless belts, such as those used on conveyance devices and more commonly referred to as conveyer belts are generally formed and/or extended around at least two driving wheels. By turning the driving wheels, the conveyer belt may be run endlessly. Conveyer belts may generally be flexible and deformable at least while running in contact with the driving wheels. A multitude of materials, linkages, and so forth have been used to achieve this end.

Conveyer belts are sometimes used in situations where x-rays and other forms of irradiation or other non-intrusive inspection techniques are used to examine objects and the insides of objects on the conveyer belt. In such situations, it is often desirable to form a conveyer belt of materials that are substantially transparent to the x-rays, other forms of irradiation, etc. so that an inspector may more clearly view the inside of the object on the conveyer belt without the conveyer belt obscuring the view. For example, airports may use a detection device at passenger entry points to check for and identify objects in luggage, bags, packages and the like. This can be a valuable step in an airport security process to ensure that passengers are not carrying objects which could be used in a harmful manner on airplanes.

Some airport security equipment for scanning baggage and the like includes a conveyor belt which passes through x-ray equipment. X-rays may be emitted from a source on one or more sides of the traversing baggage and received on an opposite side. A picture of each bag may be sent to a screen to be viewed by security personnel. The security personnel can interpret these pictures and identify any potentially harmful objects which may be in the baggage. The security equipment may further include a cage or other device to allow security personnel to access the baggage after it exits the x-ray equipment while preventing a passenger from accessing the baggage.

Often security personnel may have difficulty in quickly and accurately identifying which baggage item among several contained the potentially harmful object. Additionally, in some cases after baggage is x-rayed and an image displayed to the security personnel, if there is not another item of baggage to be scanned shortly thereafter, the image will remain on the screen at least for a short duration. Such a delay in providing a subsequent image, as well as the difficulty in accurately identifying one baggage item among many (which may be similar in appearance) can lead to confusion and passenger delay. In some instances, the baggage item desired to be inspected by the airport security personnel may exit the cage area and be picked up by a passenger before being inspected. Such a scenario can lead to re-inspection of all baggage past the security point. Flights may be delayed or canceled. Many or all would-be airline passengers may have to have their flights rebooked. Costs to an airport or airline in terms of rebooking passengers, re-inspecting baggage, and rescheduling flights can be significant.

It is desirable therefore to provide a system and method to allow security personnel to more easily identify baggage on a conveyer belt to reduce confusion, costs, and delays resulting from deficiencies in current systems.

SUMMARY

It has been recognized that it would be advantageous to develop a system and method which allows inspection personnel to more easily identify baggage on a conveyer belt to reduce confusion, costs, and delays resulting from current systems.

In accordance with an embodiment, a system for transporting objects is provided. The system can include an endless belt for transporting objects. Optically visible indicia can be associated with a position on the endless belt. Machine-detectable indicia can be on the endless belt and associated with the optically visible indicia. The machine-detectable indicia can be detected by a machine. The machine-detectable indicia can be associated with a substantially similar position on the endless belt as the optically visible indicia.

In accordance with an embodiment, an airport security system is disclosed for non-invasively inspecting baggage items. The system can include a non-invasive imaging system for providing an image of contents of a baggage item. A display device can be in communication with the non-invasive imaging system and can display the image. The system can include an endless belt for transporting baggage items through the non-invasive imaging system. Optically visible indicia can be associated with a position on the endless belt. Also, machine-detectable indicia can be associated with the optically visible indicia on the endless belt and displayable on the display device. The machine-detectable indicia can be associated with a substantially similar position on the endless belt as the optically visible indicia.

In accordance with an embodiment, a method for correlating optically visible objects with objects detectable through a non-invasive imaging system is described. The method includes conveying an object on a conveyer belt through the non-invasive imaging system. The conveyer belt can include optically visible indicia and machine-detectable indicia. The object and the machine-detectable indicia can be displayed on a display in communication with the non-invasive imaging system. The machine-detectable indicia viewed on the display can be correlated with the optically visible indicia on the conveyer belt after the object has exited the non-invasive imaging system to identify the object.

Additional features and advantages of the technology will be apparent from the detailed description which follows, taken in conjunction with the accompanying drawings, which together illustrate, by way of example, features of the technology.

DETAILED DESCRIPTION

Reference will now be made to the exemplary embodiments illustrated in the drawings, and specific language will be used herein to describe the same. It will nevertheless be understood that no limitation of the scope of the technology is thereby intended. Alterations and further modifications of the inventive features illustrated herein, and additional applications of the principles of the technology as illustrated herein, which would occur to one skilled in the relevant art and having possession of this disclosure, are to be considered within the scope of the technology.

As used herein the term "substantially" means to a great extent, a major portion, approximately, about, for the most part, or that a given property or parameter is within a small degree of variance with another property or parameter or even that the given property or parameter is the same as the another property or parameter. For example, "a substantially similar position" may refer to a same position or a position that is close.

As used herein, the term "optically visible" refers to visibility with the naked human eye. For example, "optically visible indicia" may refer to indicia visible by a human eye without the need for specialized optics, x-rays, etc.

As used herein, the term "irradiation" is used to expansively encompass the exposure to or bombardment of an object with photons, beta particles, gamma rays, ultraviolet ("uv") radiation, x-rays, computer tomography (CT) scans, sonar, and any other form of electromagnetic, radiographic, sonagraphic, and/or any other type waves or particles which may be useful for non-invasively examining an object. The term "irradiatively" is used to describe a property effectuated through irradiation. For example, "irradiately visible" may refer to the visibility of an object in an image, such as an x-ray image, where the object may or may not be optically visible.

As used herein, the term "indicia" refers to marks, signs, characters, references and other forms of indicators or designations. The term "indicia" as used herein includes both the plural form and the singular form ("indicium"). For example, indicia may refer to one or more letters, numbers, shapes, or colors.

While the following description of various aspects and embodiments of the systems and methods for transporting objects or correlating optically and irradiatively visible indicia are directed primarily towards airport security systems, the systems and methods presented herein may also be implemented in any system or industry in which conveyer belts are used to convey objects through irradiation for examination of the objects.

Airport security systems and personnel have long been using x-rays and other forms of radiography or irradiation to non-intrusively examine the contents of passenger baggage. Images of baggage contents can scroll across a screen for non-invasive inspection by airport personnel. When a single baggage item has passed through a screening device, or where there is a delay between baggage items, the last image may pause or freeze for at least a short duration on the display screen. This can cause confusion in determining whether the baggage item is still in the screening device or in a cage (which may be next to or attached to the screening device and is accessible only to airport personnel), and to confusion in identifying the correct baggage item. Frequently the conveyer belt will be run backward and forward, even up to several times, in an attempt by airport personnel to correctly identify the appropriate baggage item.

Figure 1:
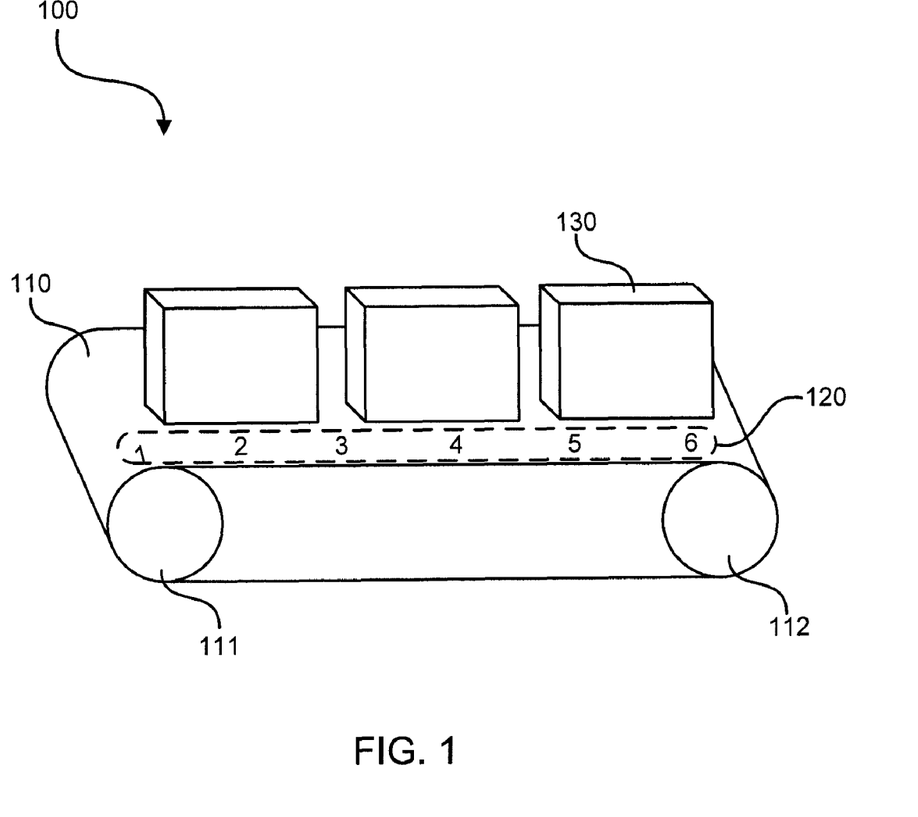
FIG. 1 is a perspective view of a conveyer belt in accordance with an embodiment.

Thus, there is a long felt need for a system and method which can allow security personnel to more easily identify baggage on a conveyer belt to reduce confusion, costs, and delays resulting from current systems. Accordingly, a system and method is provided for transporting objects. Referring to FIG. 1, a system 100 according to an embodiment comprises an endless belt 110 configured to transport objects 130. Optically visible first indicia 120 can be associated with a position on the endless belt. Rollers 111 and 112 and objects 130 are shown merely for convenience and are not necessarily a part of the system. Second indicia can be associated with the endless belt and visible by an irradiation device, the second indicia being associated with a substantially similar position on the endless belt as the first indicia. In one embodiment, such as the embodiment shown in FIG. 1, the first and second indicia can be the same indicia possessing a first quality of being optically visible and a second quality of being irradiatively visible. In other embodiments, the first and second indicia can be different indicia.

As used herein, "machine detectable" indicia includes indicia visible or detectable by an irradiation device. As will be explained in further detail below, machine detectable indicia can include a microchip or an electronic signal from a microchip which is detectable and/or readable by a computer system which may be in communication with the irradiation device.

In a more expansive view, the system may further encompass an airport security system is provided for non-invasively inspecting baggage items. The system can include an irradiation source configured to irradiate a baggage item. A detector can detect an image from irradiation through the baggage item and the image can be displayed on a display device in communication with the detector.

Figure 2:
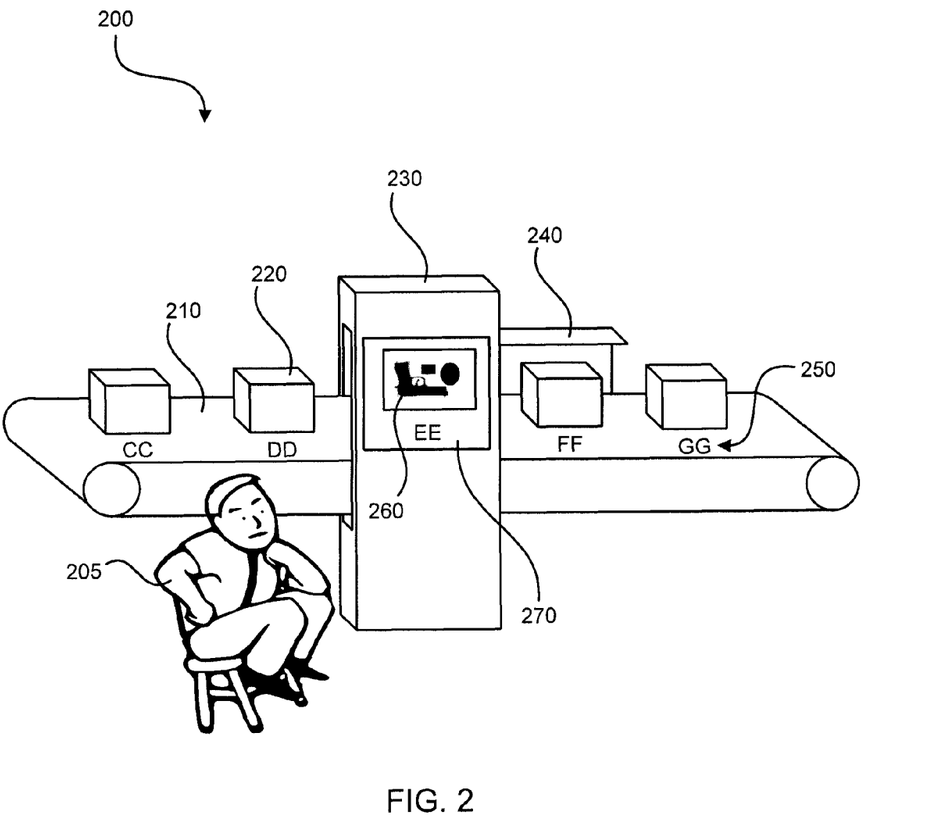
FIG. 2 is a perspective view of an airport security system for non-intrusively viewing objects inside a baggage item using a conveyer belt in accordance with an embodiment.

As illustrated in FIGS. 1-2, an endless belt, such as a conveyer belt, can be used to transport objects. In FIG. 2, the objects 220 are transported through an airport security system 200 which includes an x-ray machine 230 or other form of irradiation device. The x-ray machine includes a display 270 for displaying an image 260 produced by irradiation of objects, baggage, etc. passing through the x-ray machine. Airport security personnel 205 can view the display and observe contents of baggage and other items. The system can include a cage 240 to prevent passengers from accessing baggage items before the airport security personnel have an opportunity to access or physically inspect the baggage items when desirable or according to airport security protocol.

Some current airport security systems produce an image of items in passenger baggage where a color of the items varies depending on density of the item. For example, a higher density item may have a darker color than a lower density item. Various techniques for identifying items based on size and density are known.

A conveyer belt for airport security systems may desirably be made of low density materials or materials that are otherwise substantially transparent to the x-rays, other forms of irradiation, etc. Conveyer belts made from such materials can allow airport security personnel to more clearly view items within baggage on the conveyer belt without the conveyer belt obscuring the view. As one example, carbon filaments are sometimes used to form materials substantially transparent to at least certain forms of irradiation.

Still referring to FIG. 2, the conveyer belt 210 may include indicia 250 or other forms of identifiers for providing reference points on the conveyer belt. The indicia may include numbers (as in FIG. 1), letters (see FIG. 2), shapes, colors, symbols, patterns, a scale, or any other form of identifiable features. In one aspect, the indicia may include a set of shapes, colors, numbers, letters, symbols, etc., or combinations thereof, which may be ordered in a sequence or alternating fashion to allow distinguishment of one position on the conveyer belt from another position on the conveyer belt. In one aspect the indicia may be discrete. In one aspect, the indicia can include a set of non-repeating indicia such that, for example, a same number will not appear twice on a same belt.

In one aspect the indicia can be both optically and irradiatively visible. The indicia can be integrally formed with the belt, attached to the belt, or placed on the belt, or even on the objects on the belt. One having skill in the art may recognize a disadvantage to locating the indicia on top of an object on the belt or locating the indicia on the belt directly beneath the object as the irradiatively visible qualities of indicia may obscure at least of portion of an image produced by irradiation of the object.

The indicia may be formed of any material suitably formed to have at least one of optically and irradiatively visible qualities. Where the indicia include only one of these qualities, first and second indicia may be used where the second indicia include at least the other one of the qualities. Furthermore, placing the first and second indicia in a substantially similar position on the belt can allow for accurate correlation between the optically visible indicia and the irradiatively visible indicia. For example, first indicia may comprise a flexible metal sheet, metal mesh, or other metal linkage which is formed inside the belt. The metal qualities of the first indicia allow the first indicia to be viewed on an x-ray machine, but the first indicia are not optically visible due to formation within the belt. Accordingly, second indicia may be formed, placed, or otherwise marked on the belt to correspond with the first indicia formed within the belt. For example, the second indicia may be painted, attached, or placed over the top of the location of the first indicia within the belt.

In one aspect, the indicia may be flexible to accommodate the looping motion of the conveyer belt. The material from which the indicia are formed can vary within a set of indicia. For example, as described above, some airport security systems display items within baggage with a color representing a density of the items. Varying a density of a material from which the indicia are formed can vary the color displayed on the display. For example, a first material density may result in a blue color displayed on the display and a second material density may result in an orange color displayed on the display. The first and second materials may be dyed or otherwise colored to correspond to colors displayed on the x-ray machine according to density. In this way, airport security personnel can view a color of the indicia on the x-ray machine and correlate that to similarly colored indicia on the belt to accurately identify an object after exiting the x-ray machine.

In some embodiments, the indicia are permanently formed with or attached to the conveyer belt. In other embodiments, the indicia are placed on, removably attached to, or otherwise associated with the belt in a non-integral and/or non-permanent manner. As examples, the indicia may be: woven into the belt; formed within the belt; glued, clipped, stapled, or riveted to the inside or outside of the belt; placed on the belt; placed on a baggage item or other item on the belt; and so forth. In one aspect, the indicia are in/on a separating bar placed between objects on the conveyer belt. In another aspect, the indicia are attached to or formed with a loading container for holding objects to be irradiated. In another aspect, the indicia may be in the form of a sticker or tag which is placed on or near the belt or an object on the belt. In one aspect, multiple indicia may be attached to one another to form additional variations or combinations.

Advantageously, indicia in accordance with certain embodiments provided herein may be used with current airport security systems without replacing or retro-fitting security system equipment. In accordance with other embodiments, the system and method for indicia and correlation of optically and irradiatively visible indicia can be implemented into current airport security systems by simply replacing or retrofitting current conveyer belts to include the indicia.

Figure 3:
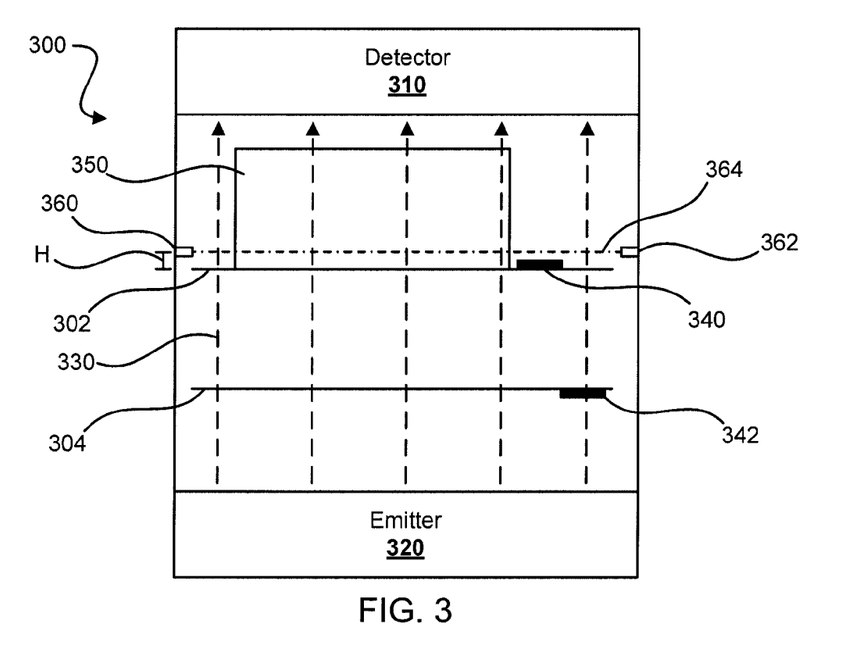
FIG. 3 is a cross-sectional side view of a transmissive system for non-intrusively viewing objects inside an object using a conveyer belt in accordance with an embodiment.

Referring to FIG. 3, a transmissive system 300 for non-intrusively viewing objects inside an object 350 using a conveyer belt 302, 304 is shown in accordance with an embodiment. The system includes an irradiation device, such as an x-ray machine for example, which includes a detector 310 and an emitter 320. X-rays 330 can be emitted by the emitter and detected by the detector. A direction and orientation of the rays as illustrated in this or other figures herein is for convenience only and is not intended to be limiting, as many irradiation systems include rays emitted at various angles, orientations, directions, etc. A cross-sectional view of the conveyer belt is shown in which a conveying portion 302 is conveying a package 350 and a return portion 304 is looping back around underneath the conveying portion.

Some airport security systems include a laser emitter and/or other form of trigger or object detection device for detecting when an object on a conveyer belt has entered the x-ray machine 300. In this way, the x-ray machine can be configured to emit x-rays only when an object is present to be scanned rather than continuously emit irradiation. For example, the x-ray machine may include a laser emitter 360, and a laser detector 362 configured to detect a laser beam 364 from the laser emitter. When the beam is obstructed by an object on the conveyer belt, for example, circuitry in the x-ray machine can cause the emitter 320 to begin emitting irradiation 330. For example, a laser beam may be directed across a conveyer belt at a predetermined distance or height H above the conveyer belt (e.g., ½ inch). Any indicia on the belt may be formed to be within or smaller than the predetermined distance or height so that the belt can continue to cycle through the machine but the x-ray machine does not emit x-rays when there is not an object on the belt to be irradiated. Without objects on the belt and indicia having a smaller profile than a laser height, x-rays are not emitted and the display screen may present a blank image. However, once an object with a profile taller than the laser height triggers the laser, x-rays may be emitted and both the object (or items within the object) and indicia can become visible on the display. The indicia in this and other figures are shown as having a profile thickness greater than a thickness of the belt and extending above a surface of the belt. However, the indicia may also be formed to have a profile of a same or even smaller thickness than the belt.

Because conveyer belts may often be formed of endless belts, and as a consequence loop around and pass underneath another portion of the belt, irradiatively visible indicia on the underside of the belt may be visible on the display of the irradiation device. Providing a proper angle of emitted irradiation or position of the irradiation source may reduce potential confusion by causing only the indicia on the top portion of the belt to be visible on the screen. For example, placing the irradiation source between the upper and lower portions of the belt may prevent indicia on the lower portion of the belt from being irradiated and displayed (generally, current airport security irradiation devices provide irradiation from the bottom up). Indicia could be positioned on the belt such that a same indicia is always on the top and bottom portions of the belt when passing through the irradiation device. Indicia can be placed at offsets in a distance from an edge of the belt to provide distinction. This example is shown in FIG. 3 where a first indicia 340 is inset from an edge of the belt and closer to a center of the belt than a second indicia 342. In other examples, indicia such as letters or numbers may have an orientation which gives indication as to which visible indicia is the proper reference indicia. For example, a letter or number on the top portion of the belt may appear to have the proper orientation as viewed on the display screen, while a letter or number on the bottom portion of the belt may appear to be backwards in orientation.

In accordance with an embodiment, a method is provided for correlating optically visible objects with objects viewable through an irradiation device. Indicia may be placed on a conveyer belt. The indicia can be visible both optically and through an irradiation device. An object can be conveyed on the conveyer belt through irradiation from an irradiation source of the irradiation device. The object and the indicia may be viewed on a display of the irradiation device. The indicia viewed on the display may be correlated with the optically visible indicia on the conveyer belt after the object has exited the irradiation device to identify the object.

Figure 4:
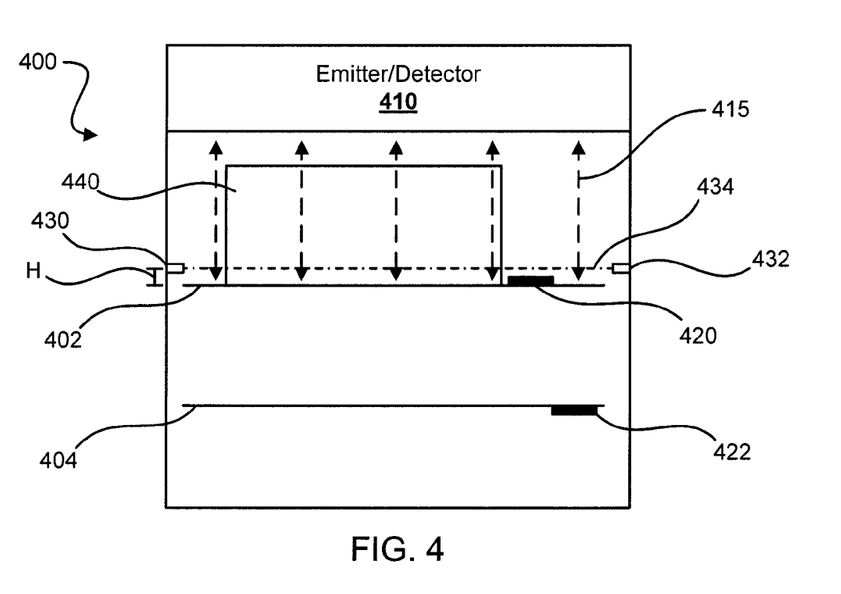
FIG. 4 is a cross-sectional side view of a system for non-invasively viewing objects inside an object using reflectivity in accordance with an embodiment.

Referring to FIG. 4, a system 400 for non-invasively viewing objects inside an object using reflectivity is shown in accordance with an embodiment. In other words, the system of FIG. 4 uses waves which are propagated from an emitter 410 and reflected off of objects 440 back to a detector 410 which may be a same or different device as the emitter in a same, similar, or nearby location. In other aspect, the waves can be reflected off in any desired direction. One example of a system using reflectivity is an ultrasound device by which sound waves 415 are "bounced" off of objects to produce an image of the object. The system of FIG. 4 can include components such as those described above in FIG. 3, including the conveying and return portions 402, 404 of the endless belt, a laser emitter 430, a laser detector 432 for detecting a laser beam 434 emitted by the emitter, multiple indicia 420, 422, and a height H between the laser and the belt.

Figure 5:
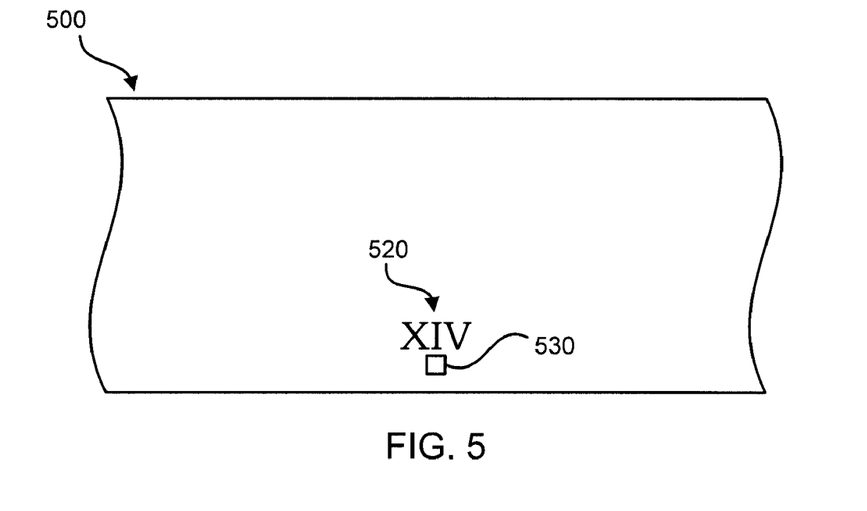
FIG. 5 is a partial top view of an endless belt including optically visible indicia and machine-detectable indicia stored on a microchip in accordance with an embodiment.

Referring to FIG. 5, a belt 500 is shown which includes indicia 520 and a microchip 530 or circuitry for storing and transmitting indicia. The belt can be endless or configured to have two or more belt ends. The microchip may comprise any form of electronic, photonic, or other type of circuitry capable of storing and transmitting indicia. For example, the microchip may comprise an radio frequency identification (RFID) tag, a transponder, a transmitter, a transceiver, etc. The indicia stored on the microchip can be an electronic equivalent of the optically visible indicia. In another example, the indicia stored on the microchip can include a different indicia than the optically visible indicia and a method for correlating the two different indicia can be provided—such as a look-up chart, for example. The microchip can be located at or near the optically visible indicia. In one example, the microchip may comprise a same shape, size, position, or other characteristic of the optically visible indicia. In another example, the microchip may comprise a small-form factor circuit which is smaller than the optically visible indicia in located in close proximity to the optically visible indicia. According to some examples, the microchip may comprise flexible circuitry to be able to bend and flex on a rotating endless belt. In another example, the microchip may be small enough that flexibility is not an issue.

The microchip and/or the indicia stored on the microchip may comprise machine-detectable indicia. Machine-detectable indicia can include the microchip and electronic information comprising the indicia, optically visible indicia, irradiatively visible indicia, and any other form of indicia which may be detectable by any form of machine.

Figure 6:
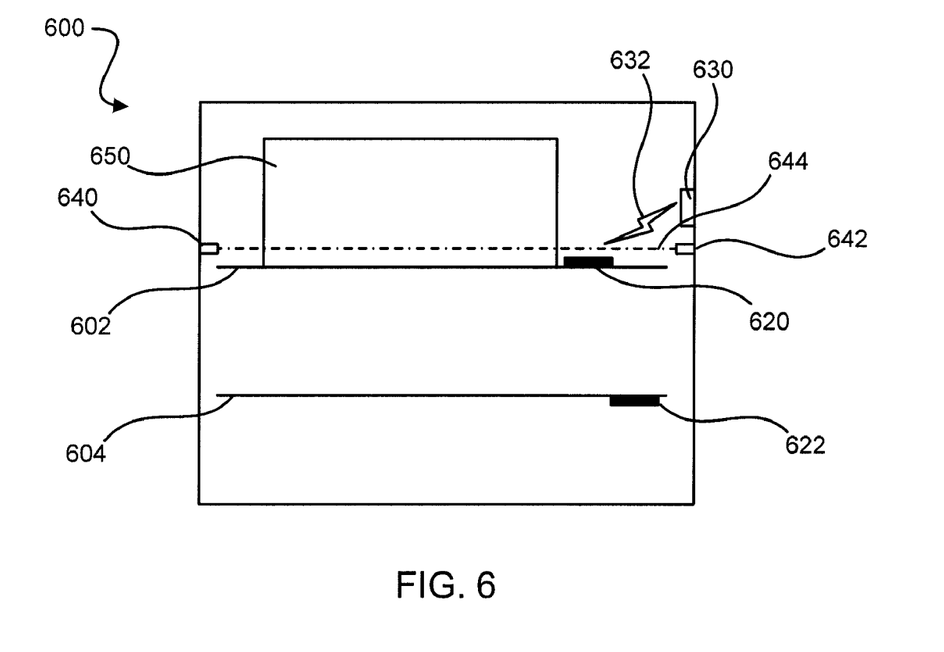
FIGS. 6-7 are cross-sectional side views of systems for electronically communicating with a microchip on an endless belt in accordance with embodiments.

Referring to FIG. 6, a microchip 620, 622 can electronically communicate with a chip reader 630, at least when the microchip is within a predetermined range of the chip reader. For example, microchip may comprise an RFID tag. The RFID tag can be an active, semi-active, or passive RFID tag. In an example where the RFID tag comprises a passive RFID tag, when the RFID tag passes through a field of a scanning antenna (e.g., on the chip reader), the RFID tag can detect an activation signal 632 from the antenna and transmit information (e.g., the indicia) stored thereon to be picked up by the scanning antenna. In an active RFID tag example, the RFID tag can include a power source and produce a stronger signal that may be readable at a greater distance than may be readable from a passive RFID tag. However, active RFID tags can be more expensive and have a shorter lifespan. In some examples, the RFID tag(s) can be configured to transmit 632 the indicia to the chip reader only when an activation signal is received. In other examples, the RFID tag(s) can be configured to continuously transmit the indicia and the indicia will only be detected when the RFID tag is within a predetermined distance from the chip reader, such as inside an irradiation device. In another example, the RFID tag(s) can be configured to emit signals including the indicia at predetermined intervals.

In some examples, a system can include multiple different machines or methods for detecting and/or identifying indicia. For example, optically visible indicia can be detected and identified visually by airport security personnel in person or via a video feed from a video camera, a still image captured by a camera, etc. Irradiatively visible indicia can be detected and identified at least using irradiation from an irradiation device and display of a resulting image. In some examples, the irradiatively visible indicia can also be optically visible and/or electronically detectable. For example, the irradiatively visible indicia may further comprise an RFID tag which is optically and irradiatively visible and is electronically detectable. The RFID tag can also be detected and/or identified by a scanner, chip reader, or the like. According to embodiments, a belt may include optically visible and electronically detectable indicia. In other embodiments, a belt may include optically visible and irradiatively visible indicia. In other embodiments, a belt may include optically visible, irradiatively visible and electronically detectable indicia. The indicia can all be one and the same or may comprise two or more different, discrete, or separate indicia. Other forms and combinations of indicia are also contemplated.

While the above discussion has focused predominantly on RFID tag microchips, the principles of using a chip attached to, placed on, or embedded in a belt to transmit an identification, such as indicia, can be implemented by any other suitable form of transmission or communication device, electronic, optical, or otherwise.

FIG. 6 further includes various components such as are present in other systems previously described. Namely, the system 600 of FIG. 6 also includes conveying and return belt portions 602, 604 of an endless belt, a laser emitter 640, a laser detector 642 for detecting a laser beam 644 emitted by the emitter, and multiple indicia 620, 622. An object 650 is shown on the belt for convenience.

Figure 7:
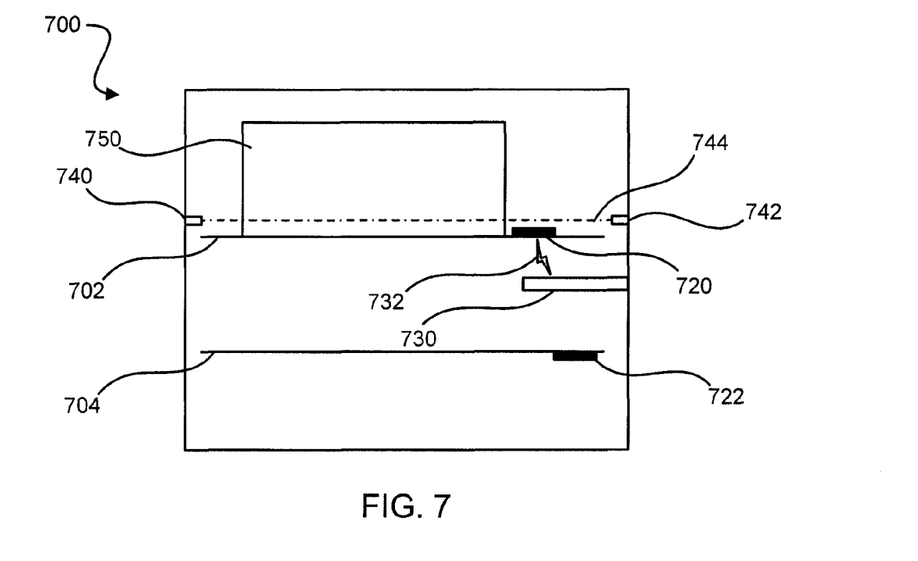

FIG. 7 is a cross-sectional side views of a system for electronically communicating with a microchip on an endless belt in accordance with embodiment and similar in many regards to the embodiment shown in FIG. 6. The system 700 of FIG. 7 includes conveying and return belt portions 702, 704 of an endless belt, a laser emitter 740, a laser detector 742 for detecting a laser beam 744 emitted by the emitter, and multiple indicia 720, 722. An object 750 is shown on the belt for convenience. Microchips 720, 722 can communicate 732 with a chip reader 730. In summary, FIG. 7 is similar in many respects to FIG. 6 and illustrates a different configuration where the chip reader is positioned to extend between the conveying and return belt portions to communicate with a microchip at least on the conveying belt portion. In contrast, the chip reader of FIG. 6 was above the conveying belt portion and did not extend outwardly from a wall of an irradiation device to overlap the belt. Numerous other configurations may also be implemented and are considered to be within the scope of this disclosure.

Figure 8:
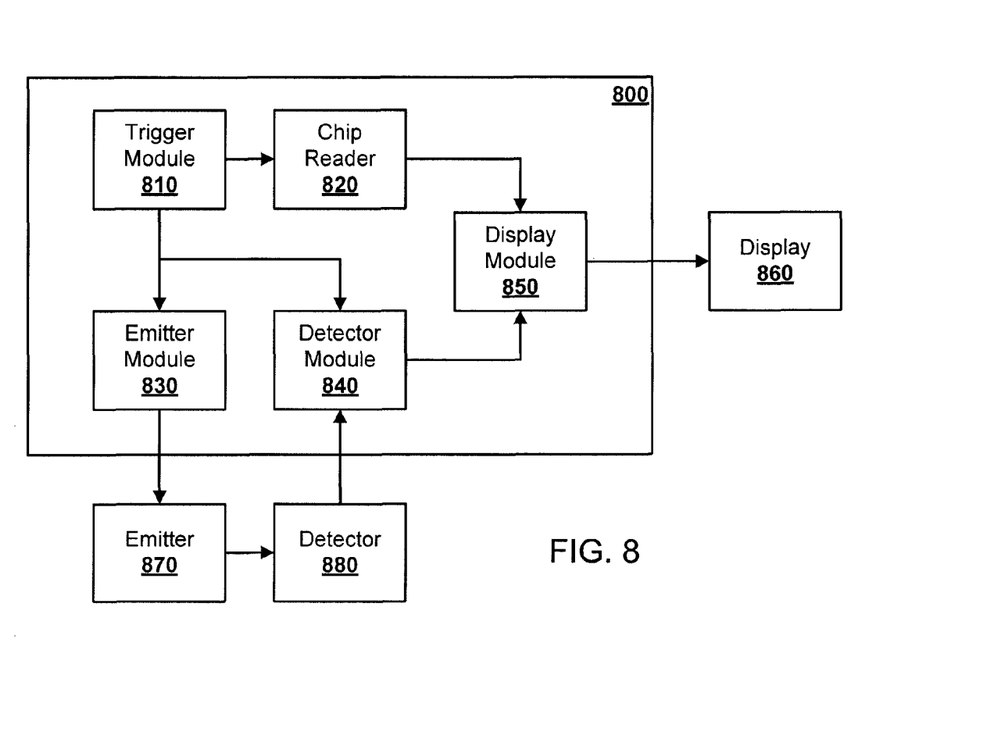
FIG. 8 is a block diagram of an electronic system for electronically communicating with a microchip in a system for non-intrusively viewing objects inside an object.

FIG. 8 is a block diagram of an electronic system 800 for electronically communicating with a microchip in a system for non-intrusively viewing objects inside an object. The system includes a trigger module 810. The trigger module can be in communication with a laser trigger system, such as that described above, or any other suitable form of triggering system. The trigger module can be in communication with a chip reader 820, an emitter module 830, and a detector module 840. When the trigger module detects or receives a triggering event, the trigger module can transmit a signal to the emitter module, which can in turn cause an emitter 870 to begin emitting irradiation. Likewise, when the trigger module detects or receives a triggering event, the trigger module can transmit a signal to the detector module, which can in turn cause a detector 880 to begin detecting irradiation. Also, in similar fashion, the trigger module can transmit the triggering event to the chip reader to begin transmitting an activation signal to a microchip. In other embodiments, the chip reader and/or the emitter and detector modules can operate independently of the trigger module. For example, the chip reader may be configured to periodically or continuously transmit an activation signal and scan for communications from a microchip.

The system 800 further includes a display module 850. The display module can be in communication with a display device 860. The display module can be configured to receive signals from the chip reader 820 and the detector module 840 to form an image to display to a user on the display device. For example, the signal from the chip reader can include the indicia received from a microchip on a belt. The signal from the detector module can include received irradiation. The display module can be configured to provide an image of an irradiated object and an image of the indicia. In one example, the image of the indicia can correspond to or be similar to the optically visible indicia on the belt. In one aspect, the image of the indicia can be overlayed on the image of the irradiated object. In another aspect, the image of the indicia can be displayed on a separate portion of the display or even on a separate display.

Figure 9:
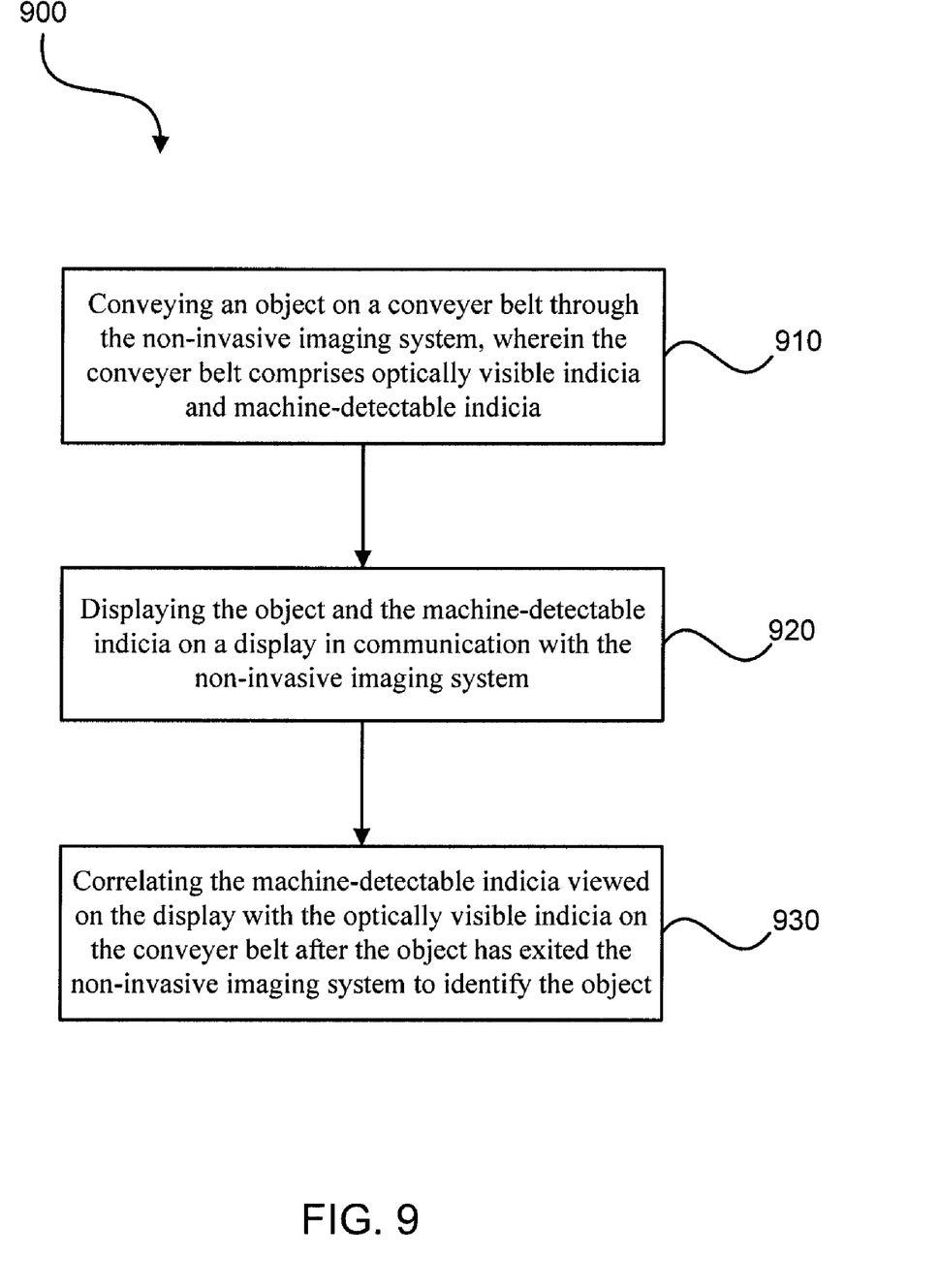
FIG. 9 is a flow diagram of a method for correlating optically visible objects with objects detectable through a non-invasive imaging system.

Referring to FIG. 9, a flow diagram of a method 900 is shown for correlating optically visible objects with objects detectable through a non-invasive imaging system. The method includes conveying 910 an object on a conveyer belt through the non-invasive imaging system. The conveyer belt can include optically visible indicia and machine-detectable indicia. The object and the machine-detectable indicia can be displayed 920 on a display in communication with the non-invasive imaging system. The machine-detectable indicia viewed on the display can be correlated 930 with the optically visible indicia on the conveyer belt after the object has exited the non-invasive imaging system to identify the object. In one example, the non-invasive imaging system comprises an x-ray imaging system and displaying the object and the machine-detectable indicia on the display comprises irradiating the object and the machine-detectable indicia, the machine-detectable indicia comprising irradiatively visible indicia.

In another example, displaying the object and the machine-detectable indicia on the display comprises irradiating the object, and receiving an electronic signal comprising the machine-detectable indicia, wherein receiving the electronic signal further comprises transmitting the electronic signal including an electronic equivalent of the optically visible indicia. In one aspect, transmitting the electronic signal further comprises transmitting the electronic signal from a transponder device attached to the conveyer belt in a substantially similar position as the optically visible indicia. In another aspect, transmitting the electronic signal further comprises transmitting the electronic signal in response to a received signal. In another aspect, transmitting the electronic signal further comprises transmitting a self-initiated electronic signal.

The method can also include attaching the machine-detectable indicia to the conveyer belt such that a vertical profile of the machine-detectable indicia is less than a height or laser triggers of the irradiation device.

The methods and systems of certain embodiments described herein may be at least partially implemented in hardware, software, firmware, or combinations thereof. In one embodiment, a method can be executed by software or firmware that is stored in a memory and that is executed by a suitable instruction execution system. If implemented in hardware, as in an alternative embodiment, the method can be implemented with any suitable technology that is well known in the art. Also within the scope of an embodiment is the implementation of a program or code that can be stored in a non-transitory machine-readable medium to permit a computer to perform any of the methods described above.

Some of the functional units described in this specification have been labeled as modules, in order to more particularly emphasize their implementation independence. The various modules, engines, tools, or modules discussed herein may be, for example, software, firmware, commands, data files, programs, code, instructions, or the like, and may also include suitable mechanisms. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

While the forgoing examples are illustrative of the principles of the present technology in one or more particular applications, it will be apparent to those of ordinary skill in the art that numerous modifications in form, usage and details of implementation can be made without the exercise of inventive faculty, and without departing from the principles and concepts of the technology. Accordingly, it is not intended that the technology be limited, except as by the claims set forth below.

What is claimed is:

1. A method for correlating optically visible objects with objects detectable through a non-invasive imaging system, comprising:
   conveying an object on a conveyer belt through the non-invasive imaging system, wherein the conveyer belt comprises optically visible indicia and machine-detectable indicia;
   displaying the object and the machine-detectable indicia on a display operatively coupled to the non-invasive imaging system;
   correlating the machine-detectable indicia viewed on the display with the optically visible indicia on the conveyer belt after the object has exited the non-invasive imaging system to identify the object.

2. A method in accordance with claim 1, wherein the non-invasive imaging system comprises an x-ray imaging system and displaying the object and the machine-detectable indicia on the display comprises irradiating the object and the machine-detectable indicia, the machine-detectable indicia comprising irradiatively visible indicia.

3. A method in accordance with claim 1, wherein displaying the object and the machine-detectable indicia on the display comprises irradiating the object, and receiving an electronic signal comprising the machine-detectable indicia, wherein receiving the electronic signal further comprises transmitting the electronic signal including an electronic equivalent of the optically visible indicia.

4. A method in accordance with claim 3, wherein transmitting the electronic signal further comprises transmitting the electronic signal from a transponder device attached to the conveyer belt in a substantially similar position as the optically visible indicia.

5. A method in accordance with claim 3, wherein transmitting the electronic signal further comprises transmitting the electronic signal in response to a received signal.

6. A method in accordance with claim 3, wherein transmitting the electronic signal further comprises transmitting a self-initiated electronic signal.

7. A method in accordance with claim 1, further comprising attaching the machine-detectable indicia to the conveyer belt such that a vertical profile of the machine-detectable indicia is less than a height of laser triggers in an irradiation device.

8. The method of claim 1, wherein the conveyor belt comprises a container placed thereon, the container including the optically visible indicia and machine-detectable indicia.

9. A system for transporting objects, comprising:
   an endless belt configured to transport objects;
   optically visible indicia associated with a position on the endless belt; and
   machine-detectable indicia associated with the optically visible indicia on the endless belt and detectable by a machine, the machine-detectable indicia being associated with a substantially similar position on the endless belt as the optically visible indicia;
   wherein the machine-detectable indicia comprises data stored on a computer chip attached to the endless belt, the machine-detectable indicia comprising an electronic equivalent of the optically visible indicia.

10. A system as in claim 9, wherein the machine-detectable indicia comprises irradiatively visible indicia, and the machine comprises an x-ray machine, wherein the machine-detectable indicia is detectable by forming an x-ray image of the irradiatively visible indicia.

11. A system as in claim 9, wherein the computer chip comprises an RFID tag.

12. A system as in claim 9, wherein the computer chip comprises a transponder.

13. A system as in claim 9, wherein the computer chip comprises an electronic transmitter.

14. A system as in claim 9, wherein the optically visible indicia comprises a letter.

15. A system as in claim 9, wherein the optically visible indicia comprises a number.

16. A system as in claim 9, wherein the optically visible indicia comprises a shape.

17. A system as in claim 9, wherein the optically visible indicia comprises a color.

18. An airport security system for non-invasively inspecting baggage items, comprising:
   a non-invasive imaging system from providing an image of contents of a baggage item;
   a display device in communication with the non-invasive imaging system and configured to display the image;
   an endless belt configured to transport baggage items through the non-invasive imaging system;
   optically visible indicia associated with a position on the endless belt; and
   machine-detectable indicia associated with the optically visible indicia on the endless belt and displayable on the display device, the machine-detectable indicia being associated with a substantially similar position on the endless belt as the optically visible indicia;
   wherein the machine-detectable indicia comprises data stored on a computer chip attached to the endless belt, the machine-detectable indicia comprising an electronic equivalent of the optically visible indicia.

19. A system as in claim 18, wherein the machine-detectable indicia comprises irradiatively visible indicia, and the non-invasive imaging system comprises an x-ray machine, wherein the machine-detectable indicia is detectable by forming an x-ray image of the irradiatively visible indicia.

* * * * *